United States Patent [19]

Wenge et al.

[11] Patent Number: 4,725,585
[45] Date of Patent: Feb. 16, 1988

[54] METHOD OF ENHANCING THE HOST DEFENSE

[75] Inventors: Per S. W. Wenge; Lena D. Håkansson, both of Upsala; Henning R. Hällgren, Bälinge, all of Sweden

[73] Assignee: Pharmacia AB, Upsala, Sweden

[21] Appl. No.: 778,560

[22] Filed: Sep. 20, 1985

Related U.S. Application Data

[63] Continuation of Ser. No. 726,956, Apr. 26, 1985, abandoned, which is a continuation of Ser. No. 455,845, Jan. 5, 1983, abandoned, which is a continuation of Ser. No. 261,800, May 8, 1981, abandoned, which is a continuation of Ser. No. 45,599, Jun. 5, 1979, abandoned.

[51] Int. Cl.⁴ ............................................. A61K 31/70
[52] U.S. Cl. ...................................... 514/54; 536/55.1
[58] Field of Search ........................... 514/54; 536/55.1

[56] References Cited

U.S. PATENT DOCUMENTS 2,850,428  9/1958  Seifter et al. ........................ 514/54
4,141,973  2/1979  Balazs ................................ 536/55.1

OTHER PUBLICATIONS

Alaverdyan, "Chem. Abst.", vol. 60, p. 2203(a).
"Scand. J. Infect. Dis. Suppl.", 24:54–57, 1980, Hakansson et al.
Hakansson et al., Reprint from "The Jour. of Clinical Investigation", vol. 66, No. 2, pp. 298–305, Aug. 1980.
Rydell, N., et al., Effect of Intra-Articular Injection of Hyaluronic Acid on the Clinical Symptoms of Arthritis in Track Horses, published in Acta Vet. Scand., vol. 11, pp. 139–155, (1970).
Algvere, P., Intravitreal Implantation of High-Molecular Hyaluronc Acid in Surgery for Retinal Detachment, published in Acta Ophthalmologica, vol. 49, pp. 975–976, (1971).
Rydell, N., et al., Effect of Intra-Articular Injection of Hyaluronic Acid on the Clinical Symptoms of Osteoarthritis and on Granulation Tissue Formation, published in Clin. Orthop., vol. 80, pp. 25–32, (1971).
Constable, Ian J., et al., Biological Vitreous Substitutes, published in Archives of Ophthalmology, vol. 88, pp. 544–548, (1972).
Balazs, E. A., et al., Hyaluronic Acid and Replacement of Vitreous and Aqueous Humor, published in Modern Problems in Ophthalmology, vol. 10, pp. 3–21, (1972).
Peyron, Jacques G., et al., Preliminary Clinical Assessment of Na–Hyaluronate Injection into Human Arthritic Joints, published in Path. Biol., vol. 22, pp. 731–736, (1974).
Rydell, N., Decreased Granulation Tissue Reaction After Installment of Hyaluronic Acid, published in Acta Orthop. Scandinav., vol. 41, pp. 307–311, (1970).
Balazs, E. A., et al., The Effect of Hyaluronic Acid on Fibroblasts, Mononuclear Phagocytes and Lymphocites, Papers of the Symposium Held in Torku, Finland, (1972).
Kulonen, E. and Pikkarainen, J., (Ed.): Biology of the Fibroblast. I, London Academic Press, p. 237, (1973).

*Primary Examiner*—Ronald W. Griffin
*Attorney, Agent, or Firm*—Stiefel, Gross, Kurland & Pavane

[57] ABSTRACT

The invention relates to a method of enhancing or regulating the host defense of a mammal, said method comprising administering to a mammal a therapeutically effective amount of hyaluronic acid.

12 Claims, No Drawings

METHOD OF ENHANCING THE HOST DEFENSE

This is a continuation of U.S. application Ser. No. 726,956, filed Apr. 26, 1985, which is a continuation of application Ser. No. 455,845, filed Jan. 5, 1983, which is a continuation of application Ser. No. 261,800, filed May 8, 1981, which is a continuation of application Ser. No. 045,599, filed June 5, 1979, now all abandoned.

The present invention relates to a method of stimulating or regulating the host defence in mammals, i.e. to fortify a mammal's resistance to infections.

In many instances it is desirable to stimulate and enhance the immunological and related systems (herein referred to as the "host defence") of mammals, especially humans, to increase the resistance to infections diseases. This would not only be desirable for patients with a reduced host defence, but also, in many instances, for patients having a normal host defence. For example, reduced resistance to infectious diseases is a common clinical problem (involving both primary and secondary defects) appearing e.g. with severly burnt patients, patients with malignancies receiving cytotoxic drugs, uremic patients, diabetics, patients suffering from chronic staphylococcus disease, chronic bronchitis, and so on. Examples of conditions where regulation of a normal host defence is desirable are e.g. immunecomplex diseases such as SLE (systemic lupus erthematosus, etc.), granulomatous diseases such as lepra, sarcoidosis, Crohn's disease, etc., malignancies, and the like.

Thus there is an urgent need for means and methods to make it possible to enhance or stimulate the host defence in mammals. However, no such means or methods are available at present.

It is an object of the present invention to solve this problem and to provide a method of enhancing or regulating the host defence in mammals.

It is another object of the invention to provide a method of preventing, inhibiting or curing diseases involving an insufficient host defence, especially the above mentioned and similar diseases.

The present invention is based on the unexpected discovery that administration of hyaluronic acid (which is a known substance) to mammals results in a considerable increase of the host defence. This effect has been confirmed by in vivo tests, as will be explained more in detail below.

The hyaluronic acid is preferably administered parenterally especially subcutaneously and also intra-muscularly or intra-venously. For parenteral administration the hyaluronic acid is preferably used in the form of a solution of a physiologically acceptable salt thereof in a physiological buffer..

The hyaluronic acid is preferably administered in doses from 1 to 40 mg, especially from 5 to 20 mg. The effect of the hyaluronic acid on the host defence usually has a rather extended duration (e.g. about one week or more), so in some cases one single administration is sufficient. In other cases repeated administrations are required, e.g. one administration each week. The suitable dose and frequency of administration can conveniently be determined in each individual case by taking blood samples from the patient for monitoring the level of host defense stimulation, e.g. by means of the procedures described below, and adjusting the dose level and administration frequency in response thereto. The treatment with hyaluronic acid in accordance with the invention has proved to be virtually without any undesired side effects.

One type of hyaluronic acid, which is suitable for the purposes of the present invention, is the essentially pur hyaluronic acid disclosed in U.S. Pat. No. 4,141,973, which is incorporated by reference herein. This hyaluronic acid has the following characteristics: an average molecular weight of at least about 750,000, a protein content of less than 0.5% by weight, ultraviolet light absorbance of a 1% solution of the sodium salt thereof of less than 3.0 at 257 nanometers wavelength and less than 2.0 at 280 nanometers wavelength, a kinematic viscosity of a 1% solution of the sodium salt thereof in physiological buffer of greater than about 1000 centistokes and a molar optical rotation of a 0.1–0.2% solution of the sodium salt thereof in physiological buffer of less than $-11 \times 10^3$ degree-cm$^2$/mole (of disaccharide) measured at 220 nanometers. Further characteristics of said hyaluronic acid fraction, which is sterile, pyrogen-free, protein-free and non-antigenic, are the absence of significant cellular infiltration of the vitreous and anterior chamber, absence of significant flare in the aqueous humor, absence of significant haze or flare in the vitreous and absence of pathological changes to the cornea, lens, iris, retina, and choroid of the owl monkey eye when on millileter of a 1% solution of the sodium salt thereof dissolved in physiological buffer is implanted in the vitreous replacing about one-half of the existing liquid vitreous. However, the invention is not intended to be restricted to the use of this specific hyaluronic acid, but any type of hyaluronic acid can be used, which is capable of causing an enhanced host response when administered to mammals in accordance with this invention.

The invention will be described more in detail in the following nonlimiting examples relating to the treatment of a plurality of patients having increased infection propensity with hyaluronic acid in accordance with the present invention. The preparation used in these Examples was Healon ®, provided by Pharmacia AB, Uppsala, Sweden. This preparation was an aqueous sterile solution for injection, 1 ml of which containing:

Sodium hyaluronate: 10 mg
Sodium chloride: 8.5 mg
Sodium dihydrogen phosphate hydrate: 0.040 mg
Disodium hydrogen phosphate dihydrate: 0.28 mg
Water: q.s.

This preparation is hereinafter referred to as "HA". The sodium hyaluronate had an average molecular weight of $1.5 \times 10^6$, a limiting viscosity of 4000 ml/g and a protein content of 0.15%. The stimulation of the host defence (neutrophil function) was monitored by kinetic studies of the phagocytic uptake of IgG or complement-coated latex particles according to the principles outlined in Hallgren et al, "Kinetic Studies of Phagocytosis of IgG-coated Latex Particles with Thrombocyte Counter", Journal of Laboratory and Clinical Medicine, Vol. 90, No. 5, pp 786–795, which is incorporated by reference herein.

EXAMPLE 1

Woman, Age 57 Years

Clinical diagnosis and symptoms before the treatment. The patient has a chronic leg wound and a strongly increased propensity to infections. She has, during the last 5 to 6 years, repeatedly suffered from bacterial infections of the meningitis, sepsis type. Since autumn 1977 she has been confined to bed with a febris continua, which has now and then been interrupted by septical fever peeks.

Phagocytosis function before the treatment. The patient had a normal phagocytosis of IgG opsonized particles, but a strongly defective ability to phagocytize serum opsonized particles. This points to a disturbance of the membrane receptor function of the neutrophil.

Treatment. The patient was given 1 ml of HA subcutaneously on the following occasions: 1 dose each week from June 13, 1978 to Oct. 1, 1979. The treatment was continued on Nov. 23, 1978 with 1 ml of HA subcutaneously ever week and was still going on (May 15, 1979).

Development after the treatment. The patient was treated and observed for 3 weeks as a patient at the University Hospital, Uppsala, Sweden. During this period the patient was still confined to bed, but the fever periods declined somewhat. The treatment was continued during the summer and she became substantially-free from infections, could be mobilized and had been at home. The treatment was continued until Oct. 1, 1978, when the patient herself requested the same to be discontinued. The effect on the leg wound had been somewhat uncertain, but the patient had no fever and was no longer confined to bed. About 3 weeks after the last injection the fever peeks of the patient became more and more frequent, and the patient requested continued treatment as she had felt better during the first period of treatment. The patient was once again hospitalized at the University Hospital, the phagocytosis function was evaluated and the treatment with hyaluronic acid was started again. About 10 days after the first injection the fever periods of the patient were once again reduced. The patient has returned to her home town and her general condition has been considerably improved. The leg wound, which has been chronic for about 6 to 7 years, is now healing.

Phagocytosis function after treatment. The granulocyte function has been normalized during the treatment, meaning that the IgG uptake is still good and that the serum dependent particle uptake has been completely normalized.

Side effects. No side effects have been discovered, except for minor skin bleedings around the points of injection.

Conclusion. This is a very ill patient with a long and serious infection anamnesis and confinement to bed for almost 1 year due to serious infections. In connection with the treatment with hyaluronic acid the patient could be mobilized and became free of fever. When the treatment was interrupted the fever periods returned. Resumption of treatment with hyaluronic acid resulted in an improvement in the patient's function subjectively and objectively.

EXAMPLE 2

Man, Age 53 Years

Clinical diagnosis and symptoms before treatment. The patient is an extremely infection sensitive individual, who has been examined and treated at various departments of the University Hospital for several years. Among other things, he has a strange lung infiltration, which sometimes has been interpreted as sarcoidosis and sometimes as a chronic fungal infection. The dominating symptoms of the patient have been very frequent bacterial infections with fever periods. Furthermore, he has developed a heart insufficiency due to cardial valve defects, and according to thorax surgical experts and cardiological experts the patient required an operation in order not to die of this disease. However, this has not been done because of the abnormal infection propensity of the patient.

Phagocytosis function before treatment. The patient has a reduced uptake both of IgG and serum opsonized particles.

Treatment. The patient has been given 1 ml of HA subcutaneously on the following occasions: Dec. 19 and 31, 1978 and Feb. 6 and 13, 1979.

Development after treatment. The patient was operated on Dec. 18, 1978 for the valve defect, and the post-operative development was completely free from infections. The patient returned to the hospital Mar. 5, 1979 since he had again had a bacterial infection, this time a sinusitis. By experience the patient's infections have been hard to treat, and the patient was therefore once again given hyaluronic acid in combination with an antibiotic. The condition of the patient was rapidly improved.

Phagocytosis function after treatment. Completely normalized.

Side effects. No side effects were observed.

Conclusion. This is an abnormally infectionprone individual, who has been tested by us several times during the last years. Because of the severe heart valve defect it was considered vital to operate on the patient. Hyaluronic acid was given in order to prevent the possible development of infections in the post-operative stage. The patient had no post-operative complications.

EXAMPLE 3

Woman, Age 37 Years

Clinical diagnosis and symptoms before treatment. The patient has a chronic bronchitis with emphysema. According to lung specialists the prognosis was ver pessimistic. The patient has had repeated pneumonic infections with fever, about 3 to 4 per month.

Phagocytosis function before treatment. Reduced phagocytosis of both IgG particles and serum opsonized particles.

Treatment. 1 ml of HA subcutaneously once every week. The treatment started Jan. 26, 1979 and was still continued on May 15, 1979.

Development after treatment. After one month of treatment the patient and her husband have experienced a subjective improvement. Compared to 3 to 4 infection periods per month the patient has during the last three months only had 1 infection episode per month.

Phagocytosis function after treatment. A considerably improved granulogyte function both with regard to the uptake of IgG and serum opsonized particles.

Side effects. No side effects observed except for a slight tenderness at the points of injection.

Conclusion. A patient with a severe bronchitis, emphysema development and a pessimistic prognosis quo ad vitam has been treated for a little more than one month with hyaluronic acid, and she has during this period experienced a clear improvement with regard to the number of infection episodes.

EXAMPLE 4

Man, Age 36 Years

Clinical diagnosis and symptoms before treatment. the patient had skin burns on both arms, caused by electricity. The total area of the burnt skin was 9%. Due to their total distruction the patient's arms were amputated. The patient had severe infections in the amputation areas.

Phagocytosis function before treatment. The phagocytosis function of the patient was monitored for two weeks. It was progressively worsened and at the end of the two week period, the phagocytosis function was very poor.

Treatment. 1 ml of HA subcutaneously on Oct. 10, 1978 and 2 ml of HA subcutaneously on Oct. 18, 1978.

Development after treatment. The general condition of the patient was very poor in relation to the size of the skin burns. The patient was in a respirator before the treatment and was dialyzed peritoneally. In connection with the treatment the patient's infected areas dried up and he could be taken out from the respirator after only a few days. The general condition was remarkably improved during the following 2 weeks and the patient was sent home 3 weeks later.

Phagocytosis function after treatment. The phagocytosis function rose somewhat after the first 1 ml injection, but then returned to the same low level. A strong increase of the uptake of both IgG and serum opsonized particles was observed after the 2 ml injection.

Side effects. None observed.

EXAMPLE 5

Man, Age 11 Years

Clinical diagnosis and symptoms before treatment. A patient with a skin burn covering 37% of the skin area. Amputation of one arm and both legs was necessary due to extended necrosis. The patient was treated in a respirator and was unconscious from the very beginning and showed symptoms of a slight cerebral atrophy.

Phagocytosis function before treatment. the phagocytosis function was followed for one week. An increasing reduction to very low levels of the uptake of both serum opsonized and IgG particles was observed.

Treatment. 1 ml of HA subcutaneously Dec. 15, 1978, 0.5 ml of HA subcutaneously Jan. 4, 1979, 1 ml of HA subcutaneously Jan. 18, 1979.

Development after treatment. The large wound areas of the patient dried up somewhat. After a while the patient woke up to consciousness and could be taken out from the respirator. He was sent to his home town hospital on Feb. 2, 1979.

Phagocytosis function after treatment. Phagocytosis of both the IgG and serum opsonized particles increased in connection with the treatments and the improvement remained for about one week after the injection.

Side effects. None observed.

Conclusion. A severely burned boy had been subjected to high tension electricity. The general condition was poor, as was the phagocytosis function before the treatment with the hyaluronic acid. In connection with this treatment the phagocytosis function was improved and the wound areas of the patient dried up. He could be sent home after about 2 months at the University Hospital.

EXAMPLE 6

Man, Age 48 Years

Clinical diagnosis and symptoms before treatment. A patient having a 25% skin burn with an initially very poor general condition and extended skin infections was studied.

Phagocytosis function before treatment. The patient had at the beginning a strong reduction of the uptake of IgG opsonized particles. The serum opsonized particle uptake diminishes progressively and after tow weeks was strongly reduced.

Treatment. 1 ml of HA subcutaneously on Feb. 9 and 16, 1979.

Development after treatment. The general condition of the patient improved very rapidly during and after the treatment. He was sent home on Mar. 7, 1979.

Phagocytosis function after treatment. A considerable improvement of the phagocytosis function after each treatment, especially with regard to the uptake of serum opsonized particles was observed.

Side effects. None observed.

Conclusion. The patient had an average size skin burn and infection complication in the wound areas. He initially had a very poor general condition and a poor phagocytosis function. Both parts were improved in connection with the treatment with hyaluronic acid.

What we claim is:

1. A method for normalizing a reduced phagocytic activity exerted by the granulocytes of a mammal, comprising administering subcutaneously or intramuscularly to said mammal a non-antigenic hyaluronic acid preparation containing hyaluronic acid or a physiologically acceptable salt of said acid in a therapeutically effective amount.

2. The method according to claim 1, wherein said effective amount comprises 1–40 mg of hyaluronic acid or a physiologically acceptable salt thereof.

3. A method for treating or preventing infections associated with reduced phagocytic activity, in mammals, comprising administering subcutaneously or intramuscularly to a mammal a therapeutically effective amount of a non-antigenic hyaluronic acid preparation containing hyaluronic acid or a physiologically acceptable salt thereof.

4. The method according to claim 3, wherein said effective amount comprises 1–40 mg of hyaluonic acid or a physiologically acceptable salt thereof.

5. The method according to claim 3, wherein the mammal to be treated exhibits reduced granulocyte phagocytic activity.

6. The method according to claim 4, wherein the mammal to be treated exhibits reduced granulocyte phagocytic activity.

7. The method claim 1, wherein the mammal is a human.

8. The method of claim 3, wherein said mammal is a human.

9. A method for treating infections in humans associated with reduced phagocytic activity, comprising administering subcutaneously or intramuscularly to a human a therapeutically effective amount of a non-antigenic hyaluronic acid or a physiologically acceptable salt thereof.

10. The method according to claim 9, wherein the human to be treated exhibits reduced granulocytic activity.

11. The method according to claim 9, wherein said effective amount comprises 1–40 mg of hyaluronic acid or a physiologically acceptable salt thereof.

12. The method according to claim 11, wherein the human to be treated exhibits reduced granulocytic activity.

* * * * *